(12) United States Patent
Liao

(10) Patent No.: US 6,605,947 B2
(45) Date of Patent: Aug. 12, 2003

(54) CUP SHAPE SENSIBLE CONTAINER FOR DETECTING LIQUID PROPERTY

(76) Inventor: Yi-Chia Liao, No. 47, Alley 93, Niu-Pu South Rd., Hsinchu (TW)

( * ) Notice: Subject to any disclaimer, the term of this patent is extended or adjusted under 35 U.S.C. 154(b) by 0 days.

(21) Appl. No.: 09/968,790

(22) Filed: Oct. 3, 2001

(65) Prior Publication Data
US 2003/0062909 A1 Apr. 3, 2003

(51) Int. Cl.[7] ............ G01N 27/02; G01N 27/416; G01R 27/08
(52) U.S. Cl. ............ 324/439; 324/693; 324/694; 324/438
(58) Field of Search ............ 324/693, 694, 324/696, 439, 438, 446, 450; 73/645, 579

(56) References Cited

U.S. PATENT DOCUMENTS

| 4,272,245 A | * | 6/1981 | Diamond et al. | 205/787.5 |
| 4,285,792 A | * | 8/1981 | McGandy | 204/402 |
| 4,301,414 A | * | 11/1981 | Hill et al. | 324/446 |
| 5,017,875 A | * | 5/1991 | Hori et al. | 324/446 |
| 5,087,883 A | * | 2/1992 | Hoffman | 324/443 |
| 5,233,860 A | * | 8/1993 | Mori et al. | 73/19.1 |
| 5,572,123 A | * | 11/1996 | Wikswo, Jr. et al. | 324/263 |
| 5,900,547 A | * | 5/1999 | Bartkiewicz | 73/447 |
| 5,918,473 A | * | 7/1999 | Gendron et al. | 62/129 |
| 5,923,259 A | * | 7/1999 | Lederer | 340/605 |
| 6,222,371 B1 | * | 4/2001 | Snyder | 324/439 |
| 6,426,629 B1 | * | 7/2002 | Edgson et al. | 324/439 |
| 6,428,689 B1 | * | 8/2002 | Kameyama et al. | 210/120 |

\* cited by examiner

Primary Examiner—N. Le
Assistant Examiner—Wasseem H Hamdan
(74) Attorney, Agent, or Firm—Birch, Stewart, Kolasch & Birch, LLP

(57) ABSTRACT

A sensible container for measuring conductive parameters in the liquid and acquiring properties of water in the liquid, consists of: a seat; a cup body installed at the seat, at least one probe being installed at a bottom of the cup body for contacting the liquid for measuring the resistance parameters of the liquid, such as concentration, pH value, salty and sugariness in the liquid; a measuring body at an interior of the seat and electrically connected to the probe for measuring the conductive parameters of the liquid; a display installed at an outer surface of the seat; and connected to the measuring body for displaying the measuring result.

2 Claims, 4 Drawing Sheets

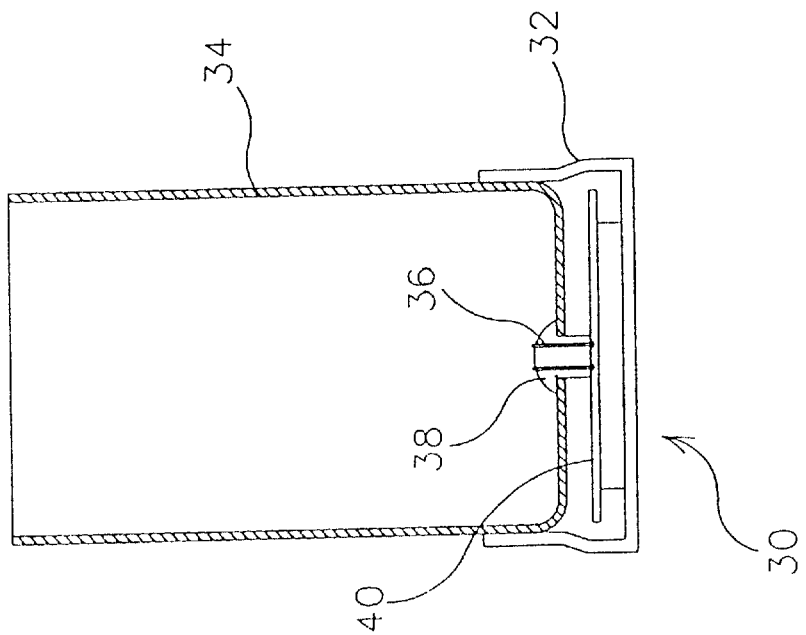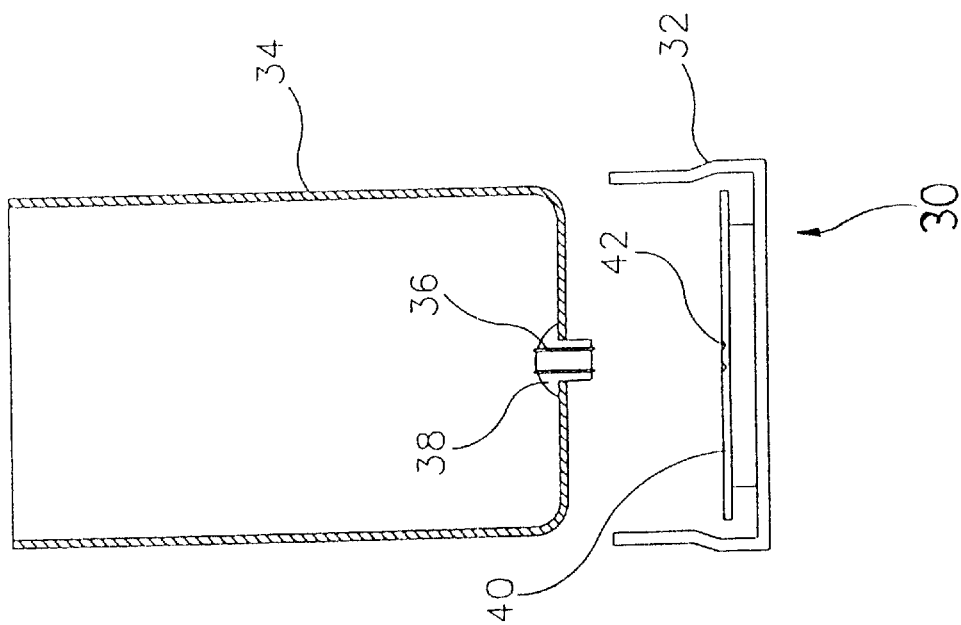

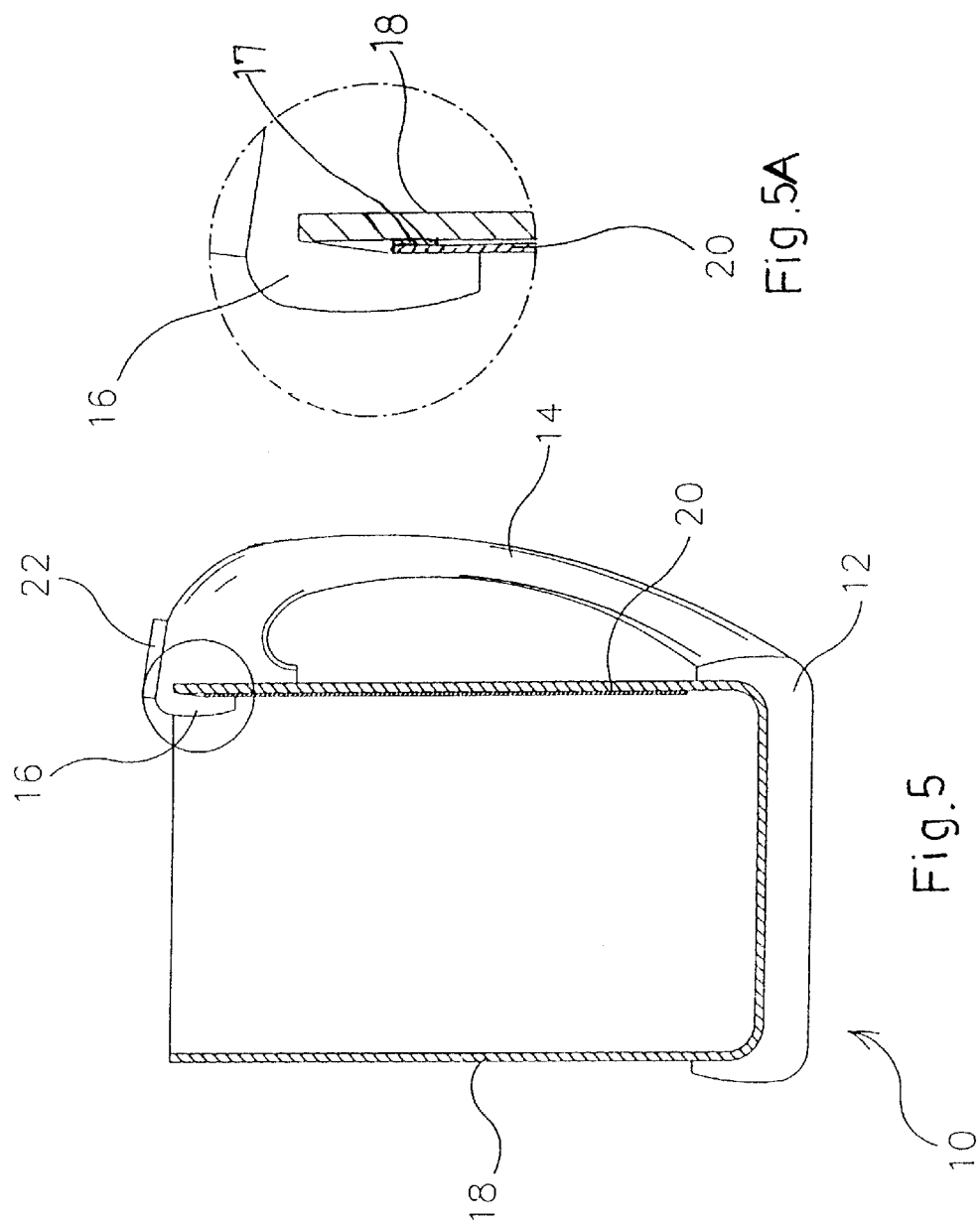

CUP SHAPE SENSIBLE CONTAINER FOR DETECTING LIQUID PROPERTY

BACKGROUND OF THE INVENTION

The present invention relates to a sensible container which can be used to be filled with liquid and detect the property of the liquid.

The prior container has only function of containing liquid for drinking or use. No other special function is designed. Therefore, if it is desired to measure the property of a liquid (such as concentrations of materials in water, pH values, salty and sugariness, others). Other detectors for detecting concentrations, pH values, salty and sugariness, etc., are necessary.

Moreover, the prior art sensor has a shape like a rod for being inserted into a container to contact with the liquid in the container. However, since the rod shape sensor is heavy, the container easily falls down and thus the liquid therein will pour out. Furthermore, the user may carry both the container and the sensor so as to induce a trouble in action.

SUMMARY OF THE INVENTION

Accordingly, the primary object of the present invention is to provide a sensible container for detecting the concentrations of materials in water, pH values, salty and sugariness, and others.

Another object of the present invention is to provide a sensible container which can be used to be filled with liquid and detect the property of the liquid.

To achieve above objects, the present invention provides a sensible container for measuring conductive parameters in the liquid and acquiring properties of water in the liquid, comprises the following components.

A seat extends upwards with a handle, and a top end of the handle is installed with a buckle.

A cup body is installed on the seat; the buckle of the handle being installed at an edge of the cup body so that the cup body serves for being filled with liquid, the inner wall of the cup body being installed with at least one probe which is capable of contacting the liquid in the cup body.

A measuring body is installed within the handle and is electrically connected to the probe for measuring a resistance parameter with the liquid.

A display is installed at a top surface of the handle to be connected to the measuring body for displaying the result from the measuring body.

The various objects and advantages of the present invention will be more readily understood from the following detailed description when read in conjunction with the appended drawing.

BRIEF DESCRIPTION OF THE DRAWINGS

FIG. 1 is an exploded view of a preferred embodiment of the present invention.

FIG. 2 is an assembled view of a preferred embodiment of the present invention.

FIG. 5 is a cross sectional view along a line 5—5 of FIG. 4.

FIG. 5A is a partial enlarged view of FIG. 5 of the present invention.

DETAILED DESCRIPTION OF THE PREFERRED EMBODIMENTS

Embodiment 1

Figure 3:
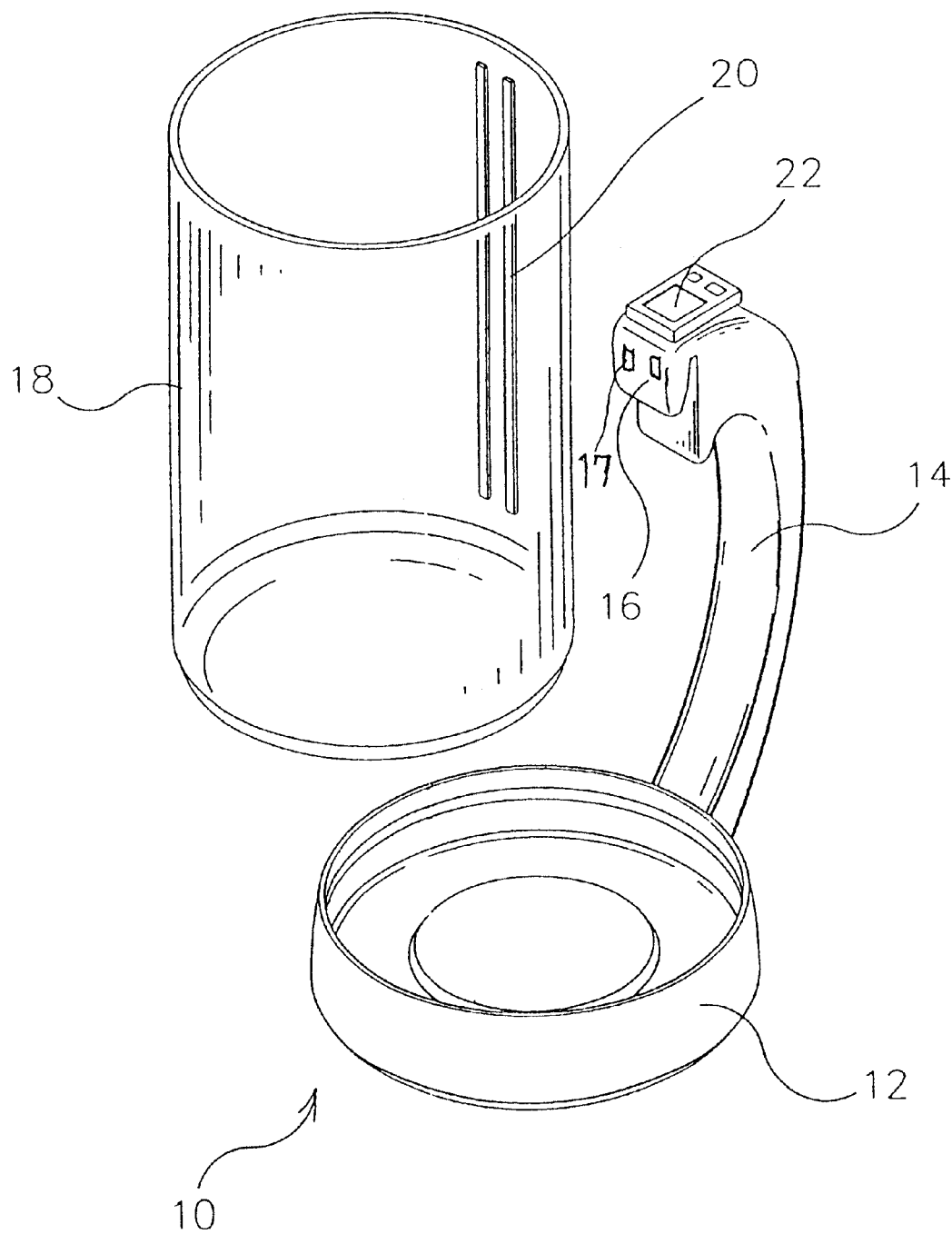
FIG. 3 is an exploded view of another embodiment in the present invention.

Referring to FIGS. 1 and 2, the exploded view and assembled view about a preferred embodiment of the present invention is illustrated.

In the present invention, a sensible container 30 is installed. The sensible container 30 includes a seat 32 having a cup body 34 thereon for being filled with water.

The bottom of the cup body 34 has two metal probes 36 for detecting the concentrations of materials in water, pH values, salty and sugariness, and others. The metal probes 36 are fixed to the bottom of the cup body 34 by a retainer 38. The metal probes are protruded from the retainer 38 to contact liquid in the cup body for checking the resistance parameters (for example, concentration, pH value, salty and sugariness in the liquid).

A measuring body 40 is in the seat 32. The measuring body 40 is installed with two conductive pieces 42 at position with respect to the two metal probes 36. By connecting the two conductive pieces 42 and the two metal probes 36, the resistance parameters in the liquid may be measured.

Moreover, a display is installed at an outer surface of the seat 32 (not shown). The display is connected to the measuring body 40 for displaying the measuring result of the measuring body 40 for being read by the user.

Embodiment 2

Figure 4:
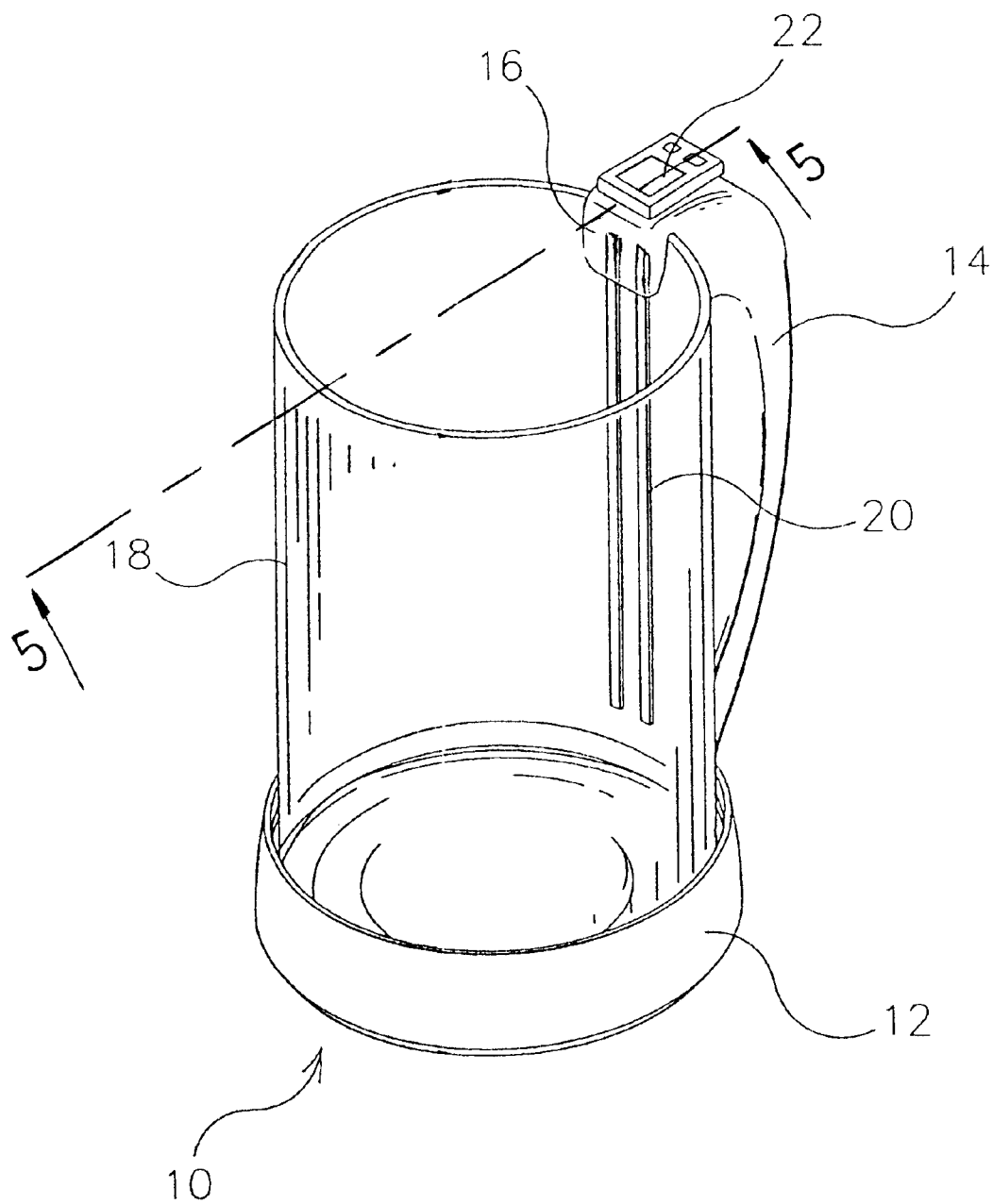
FIG. 4 is an assembled view of another embodiment of the present invention.

Referring to FIGS. 3, 4, 5, 5A, the exploded view, assembly view, cross sectional view along line 5—5 and partial enlarged view of another embodiment of the present invention is illustrated.

The sensible container 10 includes a seat 12. An edge of the seat 12 is extended with a handle 14. The top of the handle 14 is formed with a bent buckle 16.

A measuring body (not shown) is installed within the handle 14 and the measuring body has two conductive ends 17 in the buckle 16.

A cup body 18 is installed on the seat 12. The buckle 16 of the handle 14 is installed at an edge of the cup body 18 so that the cup body 18 and the handle 14 can be combined steadily. Furthermore, the inner wall of the cup body 18 is longitudinally installed with two metal probes 20 which may contact the liquid in the cup body 18.

In other words, the measuring body contacts the two metal probes 20 by the two conductive ends 17 at the inner edge of the buckle 16 for forming a conductive connection. And therefore, the conductive parameters of the liquid in the cup body 18 is measured.

Furthermore, a display 22 is installed at the bending surface of the handle 14 to be connected to the measuring body for displaying the calculating result from the measuring body on the display screen.

Other than holding by the user, the measuring body can be installed in the handle 14 to be used conveniently. The display 22 is installed at a top of the handle 14, thereby, the measuring data can be read conveniently.

In summary, the present invention has the following advantages.

1. Availability: other than supporting liquid, the sensible containers 10 and 30 can be used to check the concentration, pH value, salty and sugariness, etc.
2. The cup body can be removed from the seat for cleaning.

The present invention are thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A sensible container for measuring conductive parameters in a liquid and acquiring properties of water in the liquid, comprising:

a seat extending upwards with a handle, a top end of the handle being installed with a buckle;

a cup body installed on the seat; the buckle of the handle being installed at an edge of the cup body so that the cup body serves for being filled with the liquid; the inner wall of the cup body being installed with at least one probe which is capable of contacting the liquid in the cup body;

a measuring body being installed within the handle and being electrically connected to the probe for measuring a resistance parameter with the liquid;

a display installed at a top surface of the handle to be connected to the measuring body for displaying the result from the measuring body.

2. The sensible container as claimed in claim 1, wherein the probe is a metal probe.

* * * * *